United States Patent
Omrani

Patent Number: 5,927,278
Date of Patent: Jul. 27, 1999

[54] CONDOM SIMULATING VIRGINITY

[76] Inventor: Shahram Shawn Omrani, 11 Idaho St., Passaic, N.J. 07055-3336

[21] Appl. No.: 09/135,789

[22] Filed: Aug. 18, 1998

[51] Int. Cl.⁶ ....................................................... A61F 6/04
[52] U.S. Cl. ........................................... 128/844; 128/918
[58] Field of Search ................................... 128/842, 844, 128/918; 604/347–353

[56] References Cited

U.S. PATENT DOCUMENTS

| | | | |
|---|---|---|---|
| 2,410,460 | 11/1946 | Robinson | 128/844 |
| 4,446,860 | 5/1984 | Gutnick | 128/844 |
| 5,325,871 | 7/1994 | Reddy | 128/844 |
| 5,623,945 | 4/1997 | Shecterle | 128/844 |

*Primary Examiner*—Michael A. Brown
*Attorney, Agent, or Firm*—Terrance L. Siemens

[57] ABSTRACT

A condom for simulating conditions arising during the first sexual intercourse of a virgin woman, wherein a red fluid is released to simulate bleeding. The condom has a flexible sheath having an open end and a closed end. A closed compartment containing a red colored fluid simulating blood is disposed at the closed end. The closed compartment is fabricated from a material weaker than that of the sheath. The closed end of the sheath is preferably formed at an acute angle to the longitudinal axis of the sheath, with the closed compartment disposed forwardly and partially to the side of the front end of the sheath. Optionally, the closed compartment also contains a sponge material tending to retain some of the fluid even after rupture of the closed compartment. Preferably, the sheath and closed compartment are dark or opaque, so as to conceal the red fluid. In a further option, indicia circumscribing the sheath between the closed and open ends is provided, to indicate a suitable location for cutting the sheath, thereby converting the condom to a female repository.

8 Claims, 1 Drawing Sheet

CONDOM SIMULATING VIRGINITY

BACKGROUND OF THE INVENTION

1. Field of the Invention

The present invention relates to condoms of the type having a fluid contained within a burstable compartment.

2. Description of the Prior Art

In some cultures, virginity is demanded of a bride. Yet it is possible that a prospective bride is no longer a virgin, and hence risks being undesirable or subject to scorn and disapproval should her status become known after a marriage. In extreme cases, some cultures even sanction killing of a non-virgin bride. The applicant is unaware of apparatus which will simulate discharge of blood which ordinarily accompanies first sexual intercourse undertaken by a virgin woman, this being the effect of the present invention.

A condom which discharges a dye is seen in U.S. Pat. No. 5,411,034, issued to R. Bruce Beck et al. on May 2, 1995. The purpose of the dye is to indicate rupture of either the inner or outer layer of the subject condom. However, dyes shown in this patent are violet or deep green, and would not be suitable for simulating release of blood. Also, the inner and outer layers of the condom of Beck et al. are of equal nominal strength, and are not intended to break during sexual intercourse, as is a fluid compartment found in the present invention. There is also a virtually even likelihood that rupture, if it occurs, will affect the inner rather than outer layer in Beck et al. By contrast, the fluid compartment in the present invention contains specifically red colored fluid, is designed to break during sexual intercourse, and is disposed to release the red fluid outside the sheath of the condom.

In U.S. Pat. No. 4,795,425, issued to Bradley L. Pugh on Jan. 3, 1989, a spermicide is released both within and without the sheath of a condom if the latter is ruptured. By contrast with this arrangement, the present invention releases a red colored fluid, and is arranged to release the fluid only outside the sheath.

Condoms having burstable fluid compartments are known, and are exemplified by U.S. Pat. Nos. 4,930,522 and 5,024,852, issued to René-Guy Busnel et al. respectively on Jun. 5, 1990, and Jun. 18, 1991, U.S. Pat. No. 5,325,871, issued to Alla V. K. Reddy on Jul. 5, 1994, and U.S. Pat. No. 5,577,514, issued to Arnold S. Zimmerman on Nov. 26, 1996. In this group, fluid is released to the inside of the sheath, rather than to the outside, as seen in the present invention. Release of red colored fluid is not seen among this group of patents.

U.S. Pat. No. 5,209,242, issued to Jack W. Shields et al. on May 11, 1993, describes a condom having sponge material attached thereto outside and in front of the principal sheath. An alternative embodiment of the present invention incorporating sponge material located outside and in front of the sheath differs from the device of Shields et al. in that the sponge is enclosed rather than open. Also, the sponge is charged with red colored fluid, which feature is not taught by Shields et al.

None of the above inventions and patents, taken either singly or in combination, is seen to describe the instant invention as claimed.

SUMMARY OF THE INVENTION

The present invention provides a condom which releases a red colored fluid during sexual intercourse. The condom includes a generally conventional sheath and a burstable compartment located forwardly of the closed end of the sheath. The burstable compartment encloses a suitable fluid capable of simulating blood. Pharmacologically active substances such as spermicides may be included in the burstable compartment. The burstable compartment is formed from a material which is weaker than that of the sheath, so that it ruptures during sexual intercourse, while the sheath remains intact. The red fluid will be propagated during sexual intercourse, thereby simulating bleeding which would occur during a virgin woman's first sexual penetration.

The burstable compartment is preferably located slightly to the side of the front wall of the sheath, so that it is more likely to become pinched between the penis and the muscle walls of the vagina, thus increasing likelihood of releasing the red fluid during sexual intercourse. The burstable compartment adjoins the main sheath at the front wall of the main sheath. The front wall closes the burstable compartment at the rear, but is stronger than the material forming the rest of the burstable compartment, so that upon rupture, fluid is released to the outside of the sheath. The sheath is preferably dark colored or opaque, to conceal presence of the red fluid. This characteristic assists in concealing the simulation beforehand. Optionally, the burstable compartment contains a sponge-like material. The sponge retains the red fluid and assures that the red fluid will be distributed throughout the vagina during sexual intercourse if the burstable compartment is prematurely ruptured.

The sheath optionally has external indicia indicating a suitable location for cutting off most of the length of the sheath. This will enable converting the condom, which is provided in the form of a conventional male condom, into a female repository. The indicia is located to assure that the burstable compartment is not prematurely ruptured when cutting the condom.

Accordingly, it is a principal object of the invention to provide a condom which simulates bleeding of the first sexual intercourse of a virgin woman.

It is another object of the invention to assure wide distribution of a red colored fluid during sexual intercourse.

It is a further object of the invention to assure that fluid simulating blood be discharged to the exterior of the condom.

Still another object of the invention is that the condom conceal fluid simulating blood.

An additional object of the invention is to provide indicia indicating where to sever the condom to convert it from male form to female form.

It is again an object of the invention to promote rupture of a compartment containing fluid simulating blood under conditions of sexual intercourse and other sexual activity.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
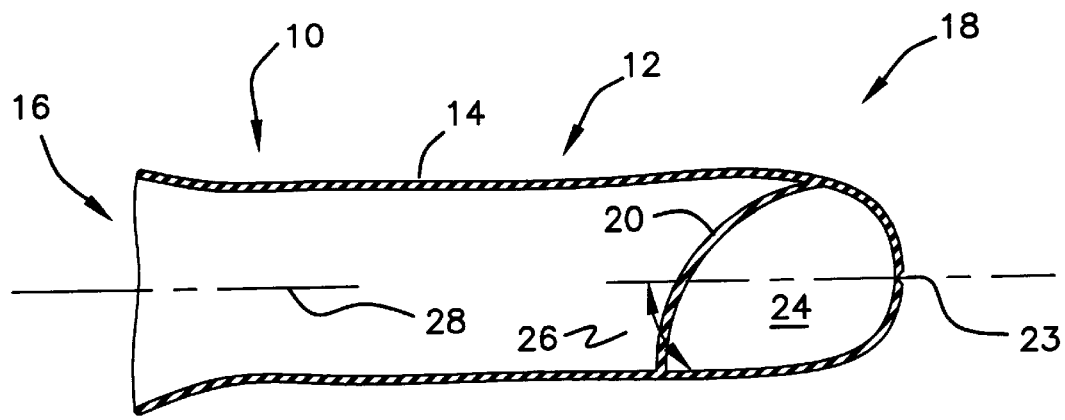
FIG. 1 is a side cross sectional view of the invention.

Turning now to FIG. 1 of the drawings, condom 10 is seen to generally comprise an elongate sheath 12 having a circumferential wall 14, an open proximal end 16, and a closed distal end 18. Sheath 12 may be fabricated from any suitable flexible material such as thin latex rubber or a synthetic equivalent. Sheath 12 may include ribs (not shown), fluid containing compartments opening to the interior of sheath 12 (none shown), and other conventional features of condoms. End wall 20 closes distal end 18. A burstable compartment 22 is attached to sheath 12, preferably forwardly (that is, to the right of end wall 20, as depicted in FIG. 1) of end wall 20. Preferably, end wall 20 is convex, opening towards compartment 22, thereby developing internal pressure acting to burst compartment 22. Circumferential wall 14 and end wall 20 are significantly stronger than is the wall of compartment 22, so that under normal conditions of sexual intercourse, compartment 22 will rupture while walls 14 and 20 will not. Preferably, compartment 22 is formed so that it will burst at the forward tip, such as at a prescored area 23.

Compartment 22 contains a fluid 24 which is colored red when exposed to view through ambient air. Fluid 24 may be permanently colored in a hue simulating human blood. A suitable material would be that employed in the motion picture industry to simulate blood. Alternatively, fluid 24 may contain a dye which reacts quickly to air to become red, even if the fluid were not red prior to exposure to air. Dyes attaining a final color after exposure to air are described in U.S. Pat. No. 5,411,034. A similarly acting dye may be employed in lieu of a permanently colored fluid, provided that the color attained upon exposure to air is a red hue simulating fresh human blood. Fluid 24 has characteristics suitable for the purpose, notably being sterile, washable, non-toxic, and generally safe for use.

Compartment 22 is burstable in that it is formed from a material having inherent predetermined strength less than that of the constituent material of sheath 12. This may be achieved in any suitable way. For example, thickness of the wall of compartment 22 may be less than that of sheath 12. Alternatively, a different material weaker than that of sheath 12 may be employed to form compartment 22. In a further alternative embodiment, the material of compartment 22 may be scored, heat treated, subjected to deleterious chemicals, or otherwise rendered more apt to rupture than is sheath 12. During sexual intercourse, compartment 22 will rupture under conditions less pronounced than those which would rupture sheath 12 and end wall 20.

End wall 20 is preferably disposed at an acute angle 26 to the longitudinal axis 28 of sheath 12. Compartment 22 abuts end wall 20, and will tend to be urged away from axis 28 during penile thrusting. This will tend to entrap compartment 22 between an erect penis and the muscle walls of the vagina, where it is more likely to be ruptured by pressure and friction, thereby distributing fluid 24, than would occur if compartment 22 remained centered at the front of condom 10.

Figure 2:
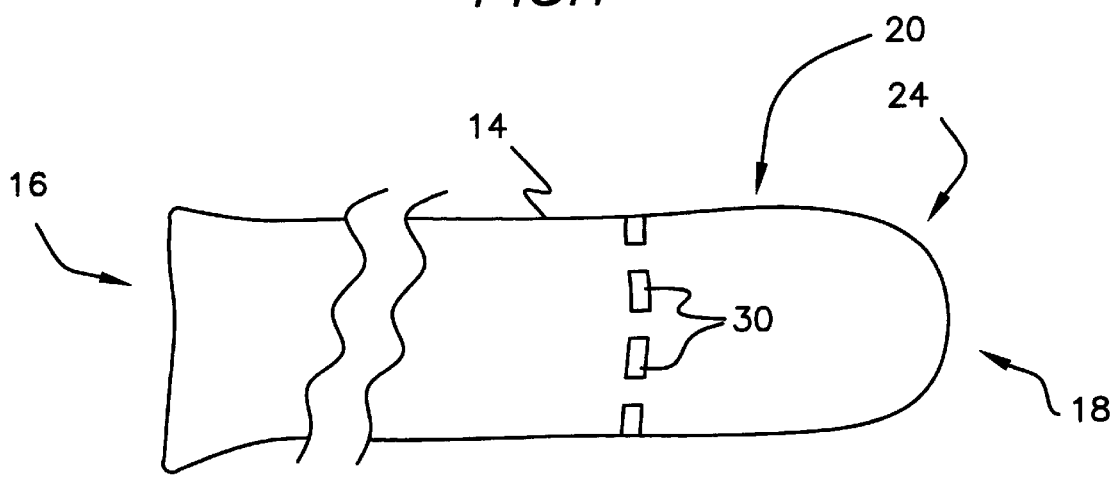
FIG. 2 is a side elevational detail view of the invention.

FIG. 2 shows two features visible at the exterior of condom 10. One is external indicia 30 discernibly disposed circumferentially about circumferential wall 14. Indicia 30 is located between end wall 20 and open end 16. The purpose of indicia 30 is to indicate a suitable location for a cut severing end 18 from end 16. If cut along indicia 30, condom 10 changes form from a male condom to a female repository. This option affords a woman the opportunity to achieve the effects made possible by the present invention without relying upon cooperation from a male sexual partner, or from a male sexual partner not wishing to wear a condom. Alternatively, that portion of condom 10 including compartment 22 may be substantially severed from sheath 12, and employed as a burstable capsule of simulated blood. The burstable capsule so obtained will be ruptured in the course of thrusting, and need not also provide function as a female repository.

A second feature shown in FIG. 2 is that sheath 12 and the exterior wall of compartment 22 have visible characteristics concealing the presence and nature of fluid 24 from view from outside condom 10. Such characteristics include opacity or, alternatively, dark color masking the actual hue of fluid 24. This feature conceals the effect of the simulated blood until such time as it would be desirable to reveal the simulated blood.

Figure 3:
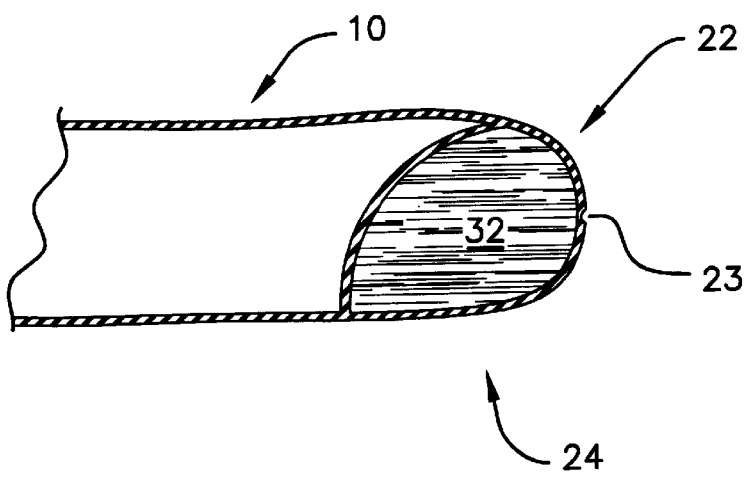
FIG. 3 is a side cross sectional detail view of an alternative embodiment of the invention.

Another optional feature of the invention is shown in FIG. 3. Compartment 22 may contain sponge material, such as an open cell synthetic polymeric foam 32, as well as fluid 24. This arrangement assures that a significant portion of fluid 24 will be retained at the forward end of condom 10 even if premature rupture of compartment 22 should occur. The consequence of this is that wide distribution of fluid 24 throughout the vagina will occur even if rupture occurs.

It is to be understood that the present invention is not limited to the embodiments described above, but encompasses any and all embodiments within the scope of the following claims.

I claim:

1. A condom capable of simulating discharge of blood during first sexual intercourse of a virgin woman, comprising:

an elongate sheath having a longitudinal axis, a flexible circumferential wall, an open proximal end, a distal end, and a convex flexible end wall disposed at an acute angle to said longitudinal axis, said flexible end wall closing said distal end;

a burstable compartment attached to the exterior of said sheath and abutting said flexible end wall, said burstable compartment being of a predetermined strength less than that of said sheath; and fluid contained within said compartment, which is released outside said sheath when pressure imposed on said burstable compartment ruptures said burstable compartment.

2. The condom according to claim 1, wherein said fluid is colored red when exposed to view through ambient air.

3. The condom according to claim 2, wherein said sheath and said burstable compartment are opaque, thus concealing said red fluid from initially being exposed to view.

4. The condom according to claim 1, wherein said burstable compartment is disposed at said distal end of said sheath and is fabricated from a thin, flexible material having a predetermined strength less than that of said sheath.

5. The condom according to claim 1, wherein said sheath has discernible external indicia disposed circumferentially about said circumferential wall for indicating a suitable location for severing said condom to convert said condom to a female repository, said indicia located between said end wall and said open end.

6. The condom according to claim 1, further including sponge material contained within said burstable compartment.

7. A condom capable of simulating discharge of blood during first sexual intercourse of a virgin woman, comprising:
- an elongate sheath having a flexible circumferential wall, a longitudinal axis, an open proximal end, a distal end, and a flexible end wall closing said distal end, said end wall disposed at an acute angle to said longitudinal axis; and
- a burstable compartment disposed at said distal end of said sheath to abut said flexible wall, said burstable compartment fabricated from a thin, flexible material having a predetermined strength less than that of said sheath, and containing a fluid which is colored red when exposed to view through ambient air and a sponge material, said burstable compartment having visible characteristics concealing said fluid which is red when exposed to view, and
- said sheath having external indicia disposed circumferentially about said circumferential wall for indicating a suitable location for severing said condom to convert said condom to a female repository, said indicia located between said end wall and said open end.

8. A method of converting a male condom to a female repository, comprising the steps of
- providing a sheath having a circumferential wall, an open end, a closed end, a burstable compartment containing a fluid, wherein the burstable compartment is disposed forwardly of the closed end, and indicia disposed circumferentially upon the circumferential wall between the open end and the closed end, to indicate a suitable location for cutting the sheath; and
- severing the sheath along the indicia so as to leave a shallow repository connected to the burstable compartment.

* * * * *